(12) United States Patent
Beymer et al.

(10) Patent No.: US 11,080,326 B2
(45) Date of Patent: Aug. 3, 2021

(54) INTELLIGENTLY ORGANIZING DISPLAYS OF MEDICAL IMAGING CONTENT FOR RAPID BROWSING AND REPORT CREATION

(71) Applicant: International Business Machines Corporation, Armonk, NY (US)

(72) Inventors: David J. Beymer, San Jose, CA (US); Ehsan Dehghan Marvast, Palo Alto, CA (US); Ahmed El Harouni, San Jose, CA (US); Girish Narayan, San Jose, CA (US); Tanveer F. Syeda-Mahmood, Cupertino, CA (US)

(73) Assignee: International Business Machines Corporation, Armonk, NY (US)

( * ) Notice: Subject to any disclaimer, the term of this patent is extended or adjusted under 35 U.S.C. 154(b) by 699 days.

(21) Appl. No.: 15/855,454

(22) Filed: Dec. 27, 2017

(65) Prior Publication Data
US 2019/0197135 A1 Jun. 27, 2019

(51) Int. Cl.
*G06F 16/54* (2019.01)
*G06T 7/00* (2017.01)
(Continued)

(52) U.S. Cl.
CPC .............. *G06F 16/54* (2019.01); *G06F 16/51* (2019.01); *G06F 16/532* (2019.01); *G06F 16/58* (2019.01);
(Continued)

(58) Field of Classification Search
None
See application file for complete search history.

(56) References Cited

U.S. PATENT DOCUMENTS

| 6,006,191 A | 12/1999 | DiRienzo |
| 8,744,149 B2 | 6/2014 | Nakamura |

(Continued)

FOREIGN PATENT DOCUMENTS

WO WO-2011122402 A1 * 10/2011 ............. G06Q 10/06

OTHER PUBLICATIONS

Kumar et al., Content-Based Medical Image Retrieval: A Survey of Applications to Multidimensional and Multimodality Data, Jul. 12, 2013, Journal of Digital Imaging, vol. 26, pp. 1025-1039 (Year: 2013).*

(Continued)

*Primary Examiner* — Devin C Hein
(74) *Attorney, Agent, or Firm* — Stephen R. Tkacs; Stephen J. Walder, Jr.; William J. Stock

(57) ABSTRACT

A mechanism is provided in a data processing system comprising a processor and a memory, the memory comprising instructions that are executed by the processor to specifically configure the processor to implement an intelligent medical image viewing engine. The intelligent medical image viewing engine receives a medical imaging study data structure comprising a plurality of electronic medical images from a medical image database. An image processing component executing within the intelligent medical image viewing engine analyzes the medical imaging study data structure to identify, for each electronic medical image in the plurality of electronic medical images, a corresponding set of image attributes. The intelligent medical image viewing engine receives a user input specifying at least one filter attribute for generating a medical image output and correlates the at least one filter attribute with at least one medical attribute of medical images to be used for selection of electronic medical images from the medical imaging study data structure. An image selection component execut- (Continued)

ing within the intelligent medical image viewing engine selects a subset of the electronic medical images in the plurality of electronic medical images based on the correlation of the at least one filter attribute with the at least one medical attribute. A user interface generation component executing within the intelligent medical image viewing engine generates and outputs a medical image output comprising the subset of electronic medical images based on the selection.

20 Claims, 4 Drawing Sheets

(51) Int. Cl.
*G16H 30/40* (2018.01)
*G06F 16/51* (2019.01)
*G06F 16/532* (2019.01)
*G16H 50/70* (2018.01)
*G16H 30/20* (2018.01)
*G16H 50/20* (2018.01)
*G06F 16/58* (2019.01)
*G16H 70/20* (2018.01)
*G06F 3/0482* (2013.01)

(52) U.S. Cl.
CPC ........... *G06T 7/0012* (2013.01); *G16H 30/20* (2018.01); *G16H 30/40* (2018.01); *G16H 50/20* (2018.01); *G16H 50/70* (2018.01); *G16H 70/20* (2018.01); *G06F 3/0482* (2013.01); *G06T 2200/24* (2013.01)

(56) References Cited

U.S. PATENT DOCUMENTS

| | | |
|---|---|---|
| 9,313,623 B1 | 4/2016 | Ledet |
| 9,430,828 B2 | 8/2016 | Wu et al. |
| 2008/0140706 A1* | 6/2008 | Kahn ..................... G06F 16/58 |
| 2012/0250961 A1 | 10/2012 | Iwasaki |
| 2013/0083894 A1 | 4/2013 | Niebler et al. |
| 2014/0043334 A1 | 2/2014 | Noshi |
| 2014/0063208 A1 | 3/2014 | Fukasawa et al. |
| 2014/0068653 A1 | 3/2014 | Ohta |
| 2016/0092656 A1 | 3/2016 | Glaser-Seidnitzer et al. |
| 2016/0124619 A1 | 5/2016 | McCallum et al. |
| 2016/0209995 A1 | 7/2016 | Jeon et al. |
| 2016/0335395 A1 | 11/2016 | Wu et al. |
| 2017/0038951 A1 | 2/2017 | Reicher et al. |
| 2017/0039321 A1 | 2/2017 | Reicher et al. |
| 2017/0039322 A1 | 2/2017 | Reicher et al. |
| 2017/0046483 A1 | 2/2017 | Reicher et al. |
| 2017/0083662 A1 | 3/2017 | Florin et al. |
| 2017/0083665 A1 | 3/2017 | Florin et al. |
| 2017/0116732 A1 | 4/2017 | Britzen |
| 2018/0301222 A1 | 10/2018 | Dew, Sr. et al. |

OTHER PUBLICATIONS

List of IBM Patents or Patent Applications Treated as Related, Dec. 11, 2018, 2 pages.
List of IBM Patents or Patent Applications Treated as Related, Mar. 8, 2018, 2 pages.
Antani, Sameer et al., "Content-Based Image Retrieval for Large Biomedical Image Archives", IMIA, MEDINFO 2004, Studies in Health and Technology Informatics, 107(Pt 2), Jan. 1, 2004, pp. 829-833.
Sluiters, E.C., "Timeline visualization of patient information for tumor board presentation", Eindhoven University of Technology, Stan Ackermans Institute, Sep. 15, 2009, 87 pages.

* cited by examiner

INTELLIGENTLY ORGANIZING DISPLAYS OF MEDICAL IMAGING CONTENT FOR RAPID BROWSING AND REPORT CREATION

BACKGROUND

The present application relates generally to an improved data processing apparatus and method and more specifically to mechanisms for intelligently organizing displays of medical imaging content for rapid browsing and report creation.

Decision-support systems exist in many different industries where human experts require assistance in retrieving and analyzing information. An example that will be used throughout this application is a diagnosis system employed in the healthcare industry. Diagnosis systems can be classified into systems that use structured knowledge, systems that use unstructured knowledge, and systems that use clinical decision formulas, rules, trees, or algorithms. The earliest diagnosis systems used structured knowledge or classical, manually constructed knowledge bases. The Internist-I system developed in the 1970s uses disease-finding relations and disease-disease relations. The MYCIN system for diagnosing infectious diseases, also developed in the 1970s, uses structured knowledge in the form of production rules, stating that if certain facts are true, then one can conclude with other facts with a given certainty factor. DXplain, developed starting in the 1980s, uses structured knowledge similar to that of Internist-I, but adds a hierarchical lexicon of findings.

Iliad, developed starting in the 1990s, adds more sophisticated probabilistic reasoning where each disease has an associated a priori probability of the disease (in the population for which Iliad was designed), and a list of findings along with the fraction of patients with the disease who have the finding (sensitivity), and the fraction of patients without the disease who have the finding (1-specificity).

In 2000, diagnosis systems using unstructured knowledge started to appear. These systems use some structuring of knowledge such as, for example, entities such as findings and disorders being tagged in documents to facilitate retrieval. ISABEL, for example, uses Autonomy information retrieval software and a database of medical textbooks to retrieve appropriate diagnoses given input findings. Autonomy Auminence uses the Autonomy technology to retrieve diagnoses given findings and organizes the diagnoses by body system. First CONSULT allows one to search a large collection of medical books, journals, and guidelines by chief complaints and age group to arrive at possible diagnoses. PEPID DDX is a diagnosis generator based on PEPID's independent clinical content.

Clinical decision rules have been developed for a number of medical disorders, and computer systems have been developed to help practitioners and patients apply these rules. The Acute Cardiac Ischemia Time-Insensitive Predictive Instrument (ACI-TIPI) takes clinical and ECG features as input and produces probability of acute cardiac ischemia as output to assist with triage of patients with chest pain or other symptoms suggestive of acute cardiac ischemia. ACI-TIPI is incorporated into many commercial heart monitors/defibrillators. The CaseWalker system uses a four-item questionnaire to diagnose major depressive disorder. The PKC Advisor provides guidance on 98 patient problems such as abdominal pain and vomiting.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a data processing system comprising a processor and a memory, the memory comprising instructions that are executed by the processor to specifically configure the processor to implement an intelligent medical image viewing engine. The method comprises receiving, by the intelligent medical image viewing engine executing in the data processing system, a medical imaging study data structure comprising a plurality of electronic medical images from a medical image database. The method further comprises analyzing, by an image processing component executing within the intelligent medical image viewing engine, the medical imaging study data structure to identify, for each electronic medical image in the plurality of electronic medical images, a corresponding set of image attributes. The method further comprises receiving, by the intelligent medical image viewing engine, a user input specifying at least one filter attribute for generating a medical image output. The method further comprises correlating, by the intelligent medical image viewing engine, the at least one filter attribute with at least one medical attribute of medical images to be used for selection of electronic medical images from the medical imaging study data structure. The method further comprises selecting, by an image selection component executing within the intelligent medical image viewing engine, a subset of the electronic medical images in the plurality of electronic medical images based on the correlation of the at least one filter attribute with the at least one medical attribute. The method further comprises generating and outputting, by a user interface generation component executing within the intelligent medical image viewing engine, a medical image output comprising the subset of electronic medical images based on the selection.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
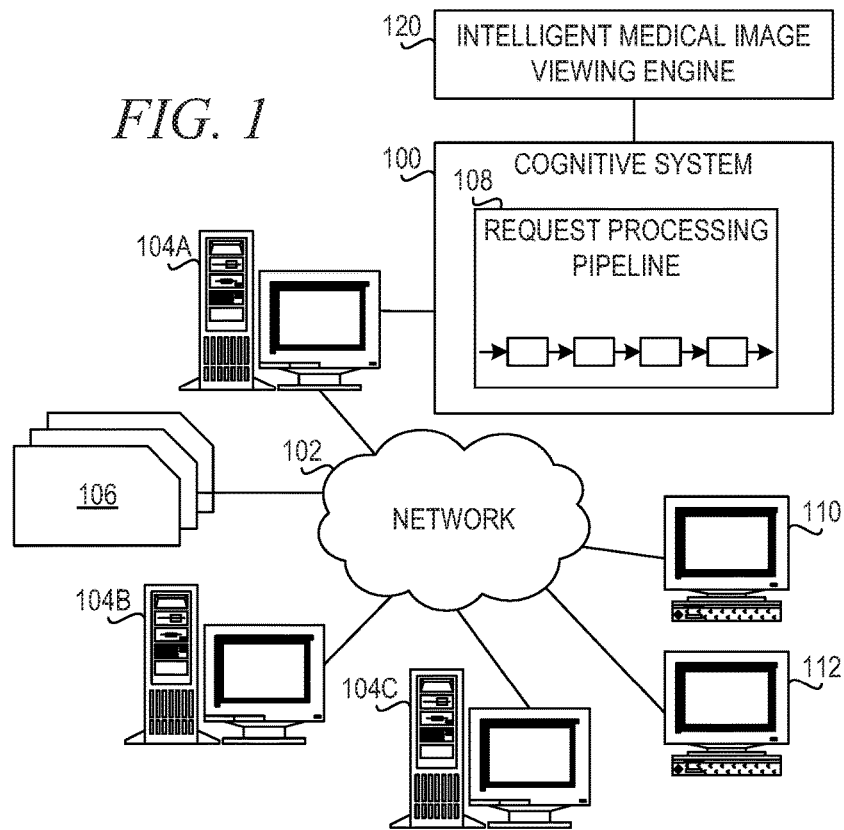
FIG. 1 depicts a schematic diagram of one illustrative embodiment of a cognitive healthcare system in a computer network.

Imaging studies are tests performed with a variety of techniques that produce pictures of the inside of a patient's body. Imaging tests are performed using sound waves, radioactive particles, magnetic fields, or x-rays that are detected and converted into images after passing through body tissues. One medical imaging study may have several imaging series, or instances, with different characteristics for each imaging series or instance. One example is a cardiac magnetic resonance imaging (MRI) study that can have several series taken with different pulse sequences (e.g., T1 T2, Steady State Free Precision (SSFP), Black Blood, etc.) and different viewpoints (e.g., short axis and log axis). Another example is echocardiography in which one study has several images with different modes (e.g., B-Mode, Color Doppler, Continuous Wave (CW), Pulse Wave (PW), M-Mode) and viewpoints (e.g., parasternal long axis view, apical views, etc.). There is also an association between anomaly/diseases and measurements and some image modes and viewpoints. An example is that a plaque in the right coronary artery (found in the report) can be seen in a right coronary artery (RCA) curved multi-planar reconstruction (MPR) CT, if available. Another example is that interventricular wall thickness is most accurately measured on a long axis parasternal B-mode image in an echocardiography study.

In the medical imaging viewer systems today, thumbnails for these images are organized in an overview page where the thumbnails are organized based on the time of acquisition. This organization is not optimal for a viewing experience because different diseases and measurements correspond to different image types and viewpoints. Thus, time of acquisition is not the most efficient methodology for organizing an imaging series in all instances.

The illustrative embodiments provide a mechanism for fast image viewing and report generation that automatically detects the type and viewpoint of the images in the images of an image series. The mechanism enables filtering, sorting, and searching by different attributes associated with diseases and measurements of interest. Thus, for example, rather than having to traverse a time series of images to find those that are most relevant to a particular criterion, the mechanism of the illustrative embodiments may identify the particular images within the series that are most relevant to the criterion and present those for viewing by the clinician. For instance, if the clinician wants to view the images from the image series that contributed to the calculation of a particular measurement, the clinician may specify the measurement of interest and the corresponding images are identified in the imaging series and presented to the clinician, rather than requiring the clinician to traverse the time series of images and identify the relevant images him/herself. The same may be true for other criteria including particular disease, abnormality, or the like.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
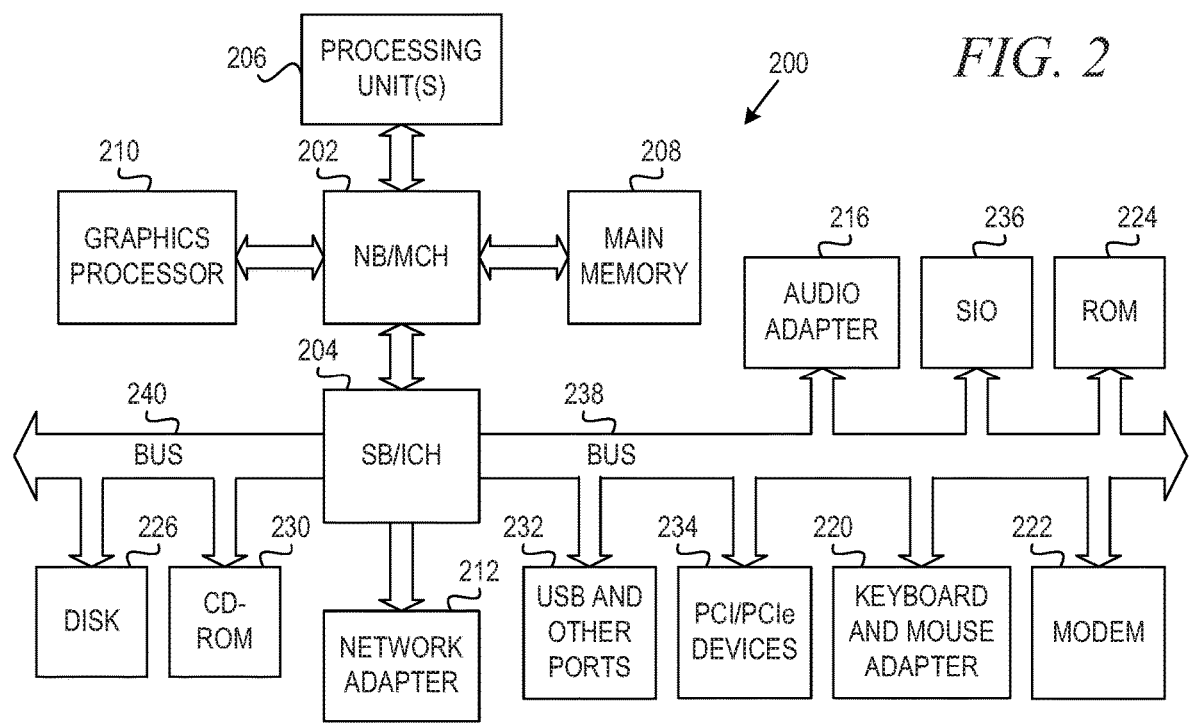
FIG. 2 is a block diagram of an example data processing system in which aspects of the illustrative embodiments are implemented.
Figure 3:
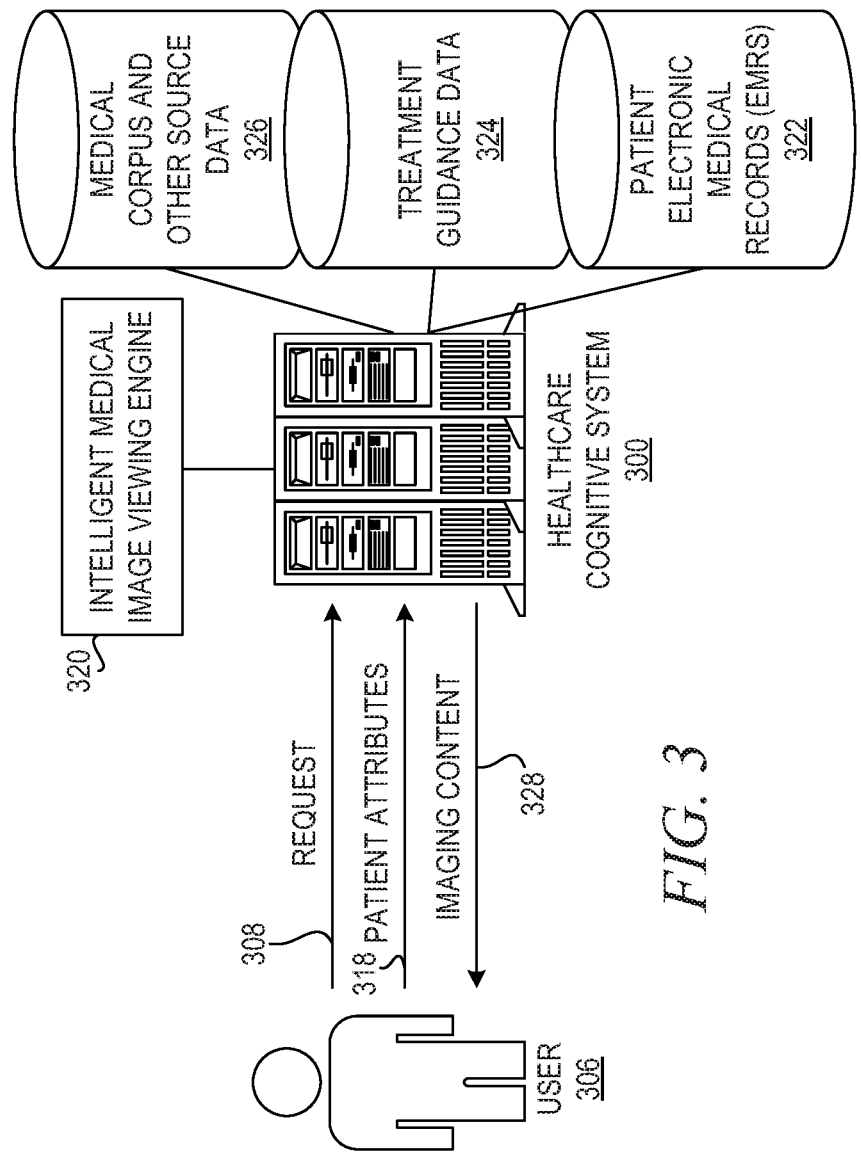
FIG. 3 is an example diagram illustrating an interaction of elements of a healthcare cognitive system in accordance with one illustrative embodiment.

As noted above, the present invention provides mechanisms for intelligently organizing displays of medical imaging content for rapid browsing and report creation. The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for healthcare applications (also referred to herein as a "healthcare cognitive system") which implements a request processing pipeline, request processing methodology, and request processing computer program product with which the mechanisms of the illustrative embodiments are implemented. These requests may be provided as structure or unstructured request messages, natural language questions, or any other suitable format for requesting an operation to be performed by the healthcare cognitive system. As described in more detail hereafter, the particular healthcare application that is implemented in the cognitive system of the present invention is a healthcare application for evaluating the completeness and data quality of electronic medical record data sources.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests, depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for cognitive analysis of EMR data, another request processing pipeline being configured for patient monitoring, etc.

Moreover, each request processing pipeline may have its own associated corpus or corpora that they ingest and operate on, e.g., one corpus for blood disease domain documents and another corpus for cancer diagnostics domain related documents in the above examples. In some cases, the request processing pipelines may each operate on the same domain of input questions but may have different configurations, e.g., different annotators or differently trained annotators, such that different analysis and potential answers are generated. The healthcare cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As will be discussed in greater detail hereafter, the illustrative embodiments may be integrated in, augment, and extend the functionality of the request processing pipeline to include mechanisms of a healthcare cognitive system with regard identifying key images from medical imaging studies based on image analysis and clinical knowledge protocols.

Thus, it is important to first have an understanding of how cognitive systems in a cognitive system implementing a request processing pipeline is implemented before describing how the mechanisms of the illustrative embodiments are integrated in and augment such cognitive systems and request processing pipeline mechanisms. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

FIG. 1 depicts a schematic diagram of one illustrative embodiment of a cognitive system 100 implementing a request processing pipeline 108 in a computer network 102. The cognitive system 100 is implemented on one or more computing devices 104A-C (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-C. The network 102 includes multiple computing devices 104A-C, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 may provide cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, sub-systems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like. For example, the cognitive system 100 receives input from the network 102, a corpus or corpora of electronic documents 106, cognitive system users, and/or other data and other possible sources of input.

In one embodiment, some or all of the inputs to the cognitive system 100 are routed through the network 102. The various computing devices 104A-C on the network 102 include access points for content creators and cognitive system users. Some of the computing devices 104A-C include devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input requests to the cognitive system 100 that are processed based on the content in the corpus or corpora of data 106. In one embodiment, the requests are formed using natural language. The cognitive system 100 parses and interprets the request via a pipeline 108, and provides a response to the cognitive system user, e.g., cognitive system user 110, containing one or more answers to the question posed, response to the request, results of processing the request, or the like. In some embodiments, the cognitive system 100 provides a response to users in a ranked list of candidate responses while in other illustrative embodiments, the cognitive system 100 provides a single final response or a combination of a final response and ranked listing of other candidate responses.

The cognitive system 100 implements the pipeline 108 which comprises a plurality of stages for processing an input request based on information obtained from the corpus or corpora of data 106. The pipeline 108 generates responses for the input question or request based on the processing of the input request and the corpus or corpora of data 106.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input request which it then parses to extract the major features of the request, which in turn are then used to formulate queries that are applied to the corpus or corpora of data 106. Based on the application of the queries to the corpus or corpora of data 106, a set of hypotheses, or candidate responses to the input request, are generated by looking across the corpus or corpora of data 106 for portions of the corpus or corpora of data 106 (hereafter referred to simply as the corpus 106) that have some potential for containing a valuable response to the input response. The pipeline 108 of the IBM Watson™ cognitive system then performs deep analysis on the language of the input question and the language used in each of the portions of the corpus 106 found during the application of the queries using a variety of reasoning algorithms.

The scores obtained from the various reasoning algorithms are then weighted against a statistical model that summarizes a level of confidence that the pipeline 108 of the IBM Watson™ cognitive system 100, in this example, has regarding the evidence that the potential candidate answer is inferred by the question. This process is be repeated for each of the candidate answers to generate ranked listing of candidate answers which may then be presented to the user that submitted the input question, e.g., a user of client computing device 110, or from which a final answer is selected and presented to the user. More information about the pipeline 108 of the IBM Watson™ cognitive system 100 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for assisting with healthcare based operations. For example, depending upon the particular implementation, the healthcare based operations may comprise patient diagnostics medical practice management systems, personal patient care plan generation and monitoring, patient electronic medical record (EMR) evaluation for various purposes. Thus, the cognitive system 100 may be a healthcare cognitive system 100 that operates in the medical or healthcare type domains and which may process requests for such healthcare operations via the request processing pipeline 108 input as either structured or unstructured requests, natural language input, or the like.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing an intelligent medical image viewing engine 120 that enables fast image viewing and report generation. Intelligent medical image viewing engine 120 automatically detects the type and viewpoint of the images in an image series. Intelligent medical image viewing engine 120 enables filtering, sorting, and searching by different attributes associated with diseases and measurements of interest.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a cognitive system 100 and cognitive system pipeline 108 augmented to include the additional mechanisms of the illustrative embodiments described hereafter.

In the depicted example, data processing system 200 employs a hub architecture including North Bridge and Memory Controller Hub (NB/MCH) 202 and South Bridge and Input/Output (I/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System P® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to provide medical imaging content for patients. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the user 306 as a human figure, the interactions with user 306 may be performed using computing devices, medical equipment, and/or the like, such that user 306 may in fact be a computing device, e.g., a client computing device. For example, interactions between the user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, the user 306 submits a request 308 to the healthcare cognitive system 300, such as via a user interface on a client computing device that is configured to allow users to submit requests to the healthcare cognitive system 300 in a format that the healthcare cognitive system 300 can parse and process. The request 308 may include, or be accompanied with, information identifying patient attributes 318. These patient attributes 318 may include, for example, an identifier of the patient 302 from which patient EMRs 322 for the patient may be retrieved, demographic information about the patient, symptoms, and other pertinent information obtained from responses to questions or information obtained from medical equipment used to monitor or gather data about the condition of the patient. Any information about the patient that may be relevant to a cognitive evaluation of the patient by the healthcare cognitive system 300 may be included in the request 308 and/or patient attributes 318.

The healthcare cognitive system 300 provides a cognitive system that is specifically configured to perform an implementation specific healthcare oriented cognitive operation. In the depicted example, this healthcare oriented cognitive operation is directed to providing a medical imaging content 328 to the user 306 to assist the user 306 in treating the patient based on their reported symptoms and other information gathered about the patient. The healthcare cognitive system 300 operates on the request 308 and patient attributes 318 utilizing information gathered from the medical corpus and other source data 326, treatment guidance data 324, and the patient EMRs 322 associated with the patient to generate imaging content 328.

In accordance with the illustrative embodiments herein, the healthcare cognitive system 300 is augmented to include an intelligent medical image viewing engine 320 that enables fast image viewing and report generation that automatically detects the type and viewpoint of the images in an image series. Intelligent medical image viewing engine 320 enables filtering, sorting, and searching by different attributes associated with diseases and measurements of interest. Thus, for example, rather than having to traverse a time series of images to find those images that are most relevant to a particular criterion, intelligent medical image viewing engine 320 may identify the particular images within the series that are most relevant to the criterion and present those for viewing by the clinician. For instance, if the clinician wants to view the images from the image series that contributed to the calculation of a particular measurement, the clinician may specify the measurement of interest and the corresponding images are identified in the imaging series and presented to the clinician, rather than requiring the clinician to traverse the time series of images and identify the relevant images. The same may be true for other criteria including particular disease, abnormality, or the like.

Figure 4:
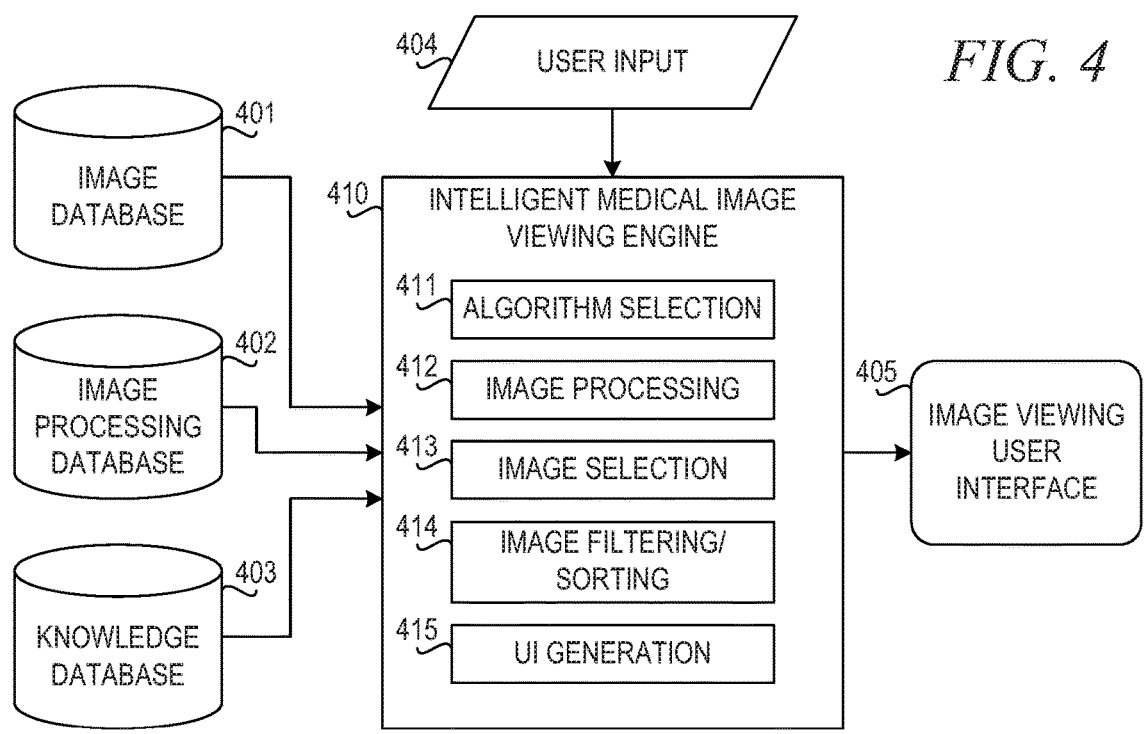
FIG. 4 is a block diagram illustrating a system for intelligently organizing displays of medical imaging content for rapid browsing and report generation in accordance with an illustrative embodiment.

FIG. 4 is a block diagram illustrating a system for intelligently organizing displays of medical imaging content for rapid browsing and report generation in accordance with an illustrative embodiment. The system includes an image and report database 401, which holds the study images and the corresponding reports, if available. Image and report database 401 may hold information from patient EMRs database 322 in FIG. 3.

Image processing database 402 holds the algorithms necessary to detect the mode and viewpoint and/or other attributes and properties of images, such as valve recognition. These processing algorithms may include the following:

A text processing algorithm using DICOM tags as input.
A text/natural language processing algorithm using the image report as input.
Image processing algorithms using the image data as input.
Machine learning algorithms including deep learning using the image data as input.

Digital Imaging and Communications in Medicine (DICOM) is a standard for handling, storing, printing, and transmitting information in medical imaging. DICOM includes a file format definition and a network communications protocol. The communication protocol is an application protocol that uses Transport Control Protocol/Internet Protocol (TCP/IP) to communicate between systems.

Knowledge database 403 stores information about different diseases and measurements and their corresponding image modes or viewpoints. As an example, knowledge database 403 may have information showing that interventricular septum is measured on a parasternal long axis B-mode echocardiogram. Another example is that infarction can be seen in a delayed enhancement MRI image. This knowledge may be gathered by mining clinical guidelines or other forms of literature, such as treatment guidance data 324 or medical corpus and other source data 326, or entered into the system by experts. Knowledge database 403 may store the correlation information in any data structure format, such as table, extensible markup language (XML), or the like. Furthermore, the knowledge information may specify which text processing, natural language processing, image processing, or machine learning algorithms are best for detecting the imaging mode or viewpoint that correlates with a given abnormality or disease.

During the image viewing experience, a user may provide user input 404 to intelligent medical image viewing engine 410. The user may have the option to sort, filter, or search images based on their mode, viewpoint, or corresponding measurement and abnormality or disease. Thus, user input 404 may indicate an abnormality or disease. Diseases or abnormalities may be mentioned in image reports, and intelligent medical image viewing engine 410 may present a list of diseases or abnormalities for selection through user input 404.

Intelligent medical image viewing engine 410 includes algorithm selection component 411, image processing component 412, image selection component 413, image filtering component 414, and image sorting component 415. Algorithm selection component 411 consults knowledge database 403 based on the user input 404 to identify the imaging modes or viewpoints that correspond to the abnormality or disease specified in user input 404. Algorithm selection component 411 then identifies the image processing algorithms from image processing database 402 to apply to the image sequences in image database 401 based on the imaging modes or viewpoints that correlate to the abnormality or disease specified in user input 404.

The algorithms in illustrative embodiments determine image mode, view point, or valve. In one embodiment all of these can be pre-determined, before input from user, and saved to a database. Upon input from the user, the proper images will be retrieved. For example, mode and view point of echocardiograms can be pre-determined with the algorithms and saved into a database. Then, if the input from the user is "Interventricular Septum," the system consults with the knowledge databased and realizes that the image to be retrieved is a B-Mode with Parasternal long Axis view. Then, the system searches the database for images based on the image modes and viewpoints and retrieves the right images.

Image processing component 412 applies image processing algorithms from image processing database 402 to detect a mode, viewpoint, or valve of images. The image processing algorithms may include text processing algorithms using the DICOM tags as input, text/natural language processing algorithms using the image report as input, image processing algorithms using the image data as input, or machine learning algorithms, including deep learning, using the image data as input. There are different image processing algorithms to do this classification for different modalities or to detect viewpoints of images of different modes, for example. As mentioned, the images can be pre-processed and the results can be saved in a database (even in DICOM database). Knowledge database 403 correlates these attributes to diseases and measurements.

Image selection component 413 selects images for inclusion in the display of medical imaging content or for report creation based on the results of image processing.

Image filtering/sorting component 414 enables the user to filter or sort the selected medical images. For example, for a case of echocardiography, the user can filter and sort images based on their modes (e.g., B-Mode, Color Doppler, M-Mode, CW and PW Doppler, etc.), based on their viewpoints (e.g., parasternal long and short axis, Apical 3, 4, 5 chamber view, etc.), or by selecting any normal or abnormal measurements found in the corresponding text report or the DICOM Structured Report (SR). Also, diseases mentioned in the report, if available, can be used to select images using the disease/viewpoint correspondence in the knowledge database 403. For example, if aortic stenosis is reported in an echocardiogram report, it will appear as a selection tool in the viewer and by selecting this disease CW and Doppler images of the aortic valve will be shown.

User interface (UI) generation component 415 generates image viewing user interface 405, which intelligently organizes the display of the selected medical images for rapid browsing. Image viewing user interface 405 presents the selected medical images so the user does not have to traverse a time series of images to identify the relevant images. Image viewing user interface 405 may also include a user interface element for entering search terms, such as diseases, abnormalities, filtering attributes, or sorting criteria. Image viewing user interface 405 may also include user interface elements for selecting filtering attributes or sorting criteria.

Figure 5:
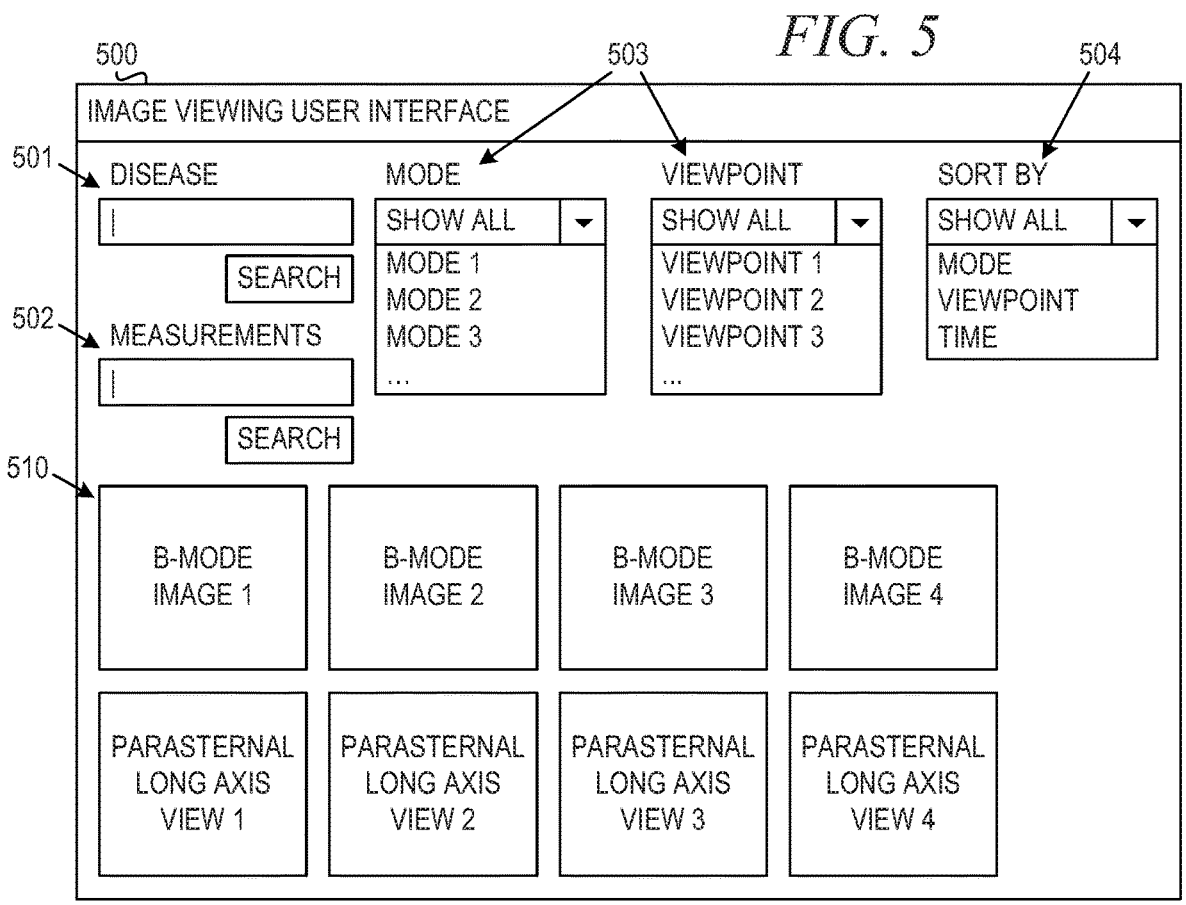
FIG. 5 depicts an example image viewing user interface in accordance with an illustrative embodiment.

FIG. 5 depicts an example image viewing user interface in accordance with an illustrative embodiment. Image viewing user interface 500 presents selected images 510, which are selected as being the most relevant images for a given disease or abnormality for which a patient is being examined. Image viewing user interface 500 also includes a user interface element 501, which is a search field enabling the user to enter a disease (or abnormality). User interface element 502 is a search field enabling the user to enter measurements to be shown in selected images 510.

User interface elements 503 are drop-down lists enabling the user to select from a plurality of modes or viewpoints. In one embodiment, user interface elements 503 list modes or viewpoints that exist in the selected images 510, thus enabling the user to filter the images to only the selected mode or viewpoint. In another embodiment, the user may filter all images to a particular mode or viewpoint.

User interface element 504 is a drop-down list enabling the user to select a sort criterion for sorting the relevant images 510. In the depicted example, the sort criteria include sorting by mode, viewpoint, or time.

In one example embodiment, the user may then enter a disease via user interface element 501, may select a mode and/or viewpoint via user interface elements 503, and may select a sort criterion via user interface element 504. In response, images 510 are presented that correspond to the selected disease, filtered based on the selected mode and/or viewpoint, and sorted according to the selected sorting criterion.

Figure 6:
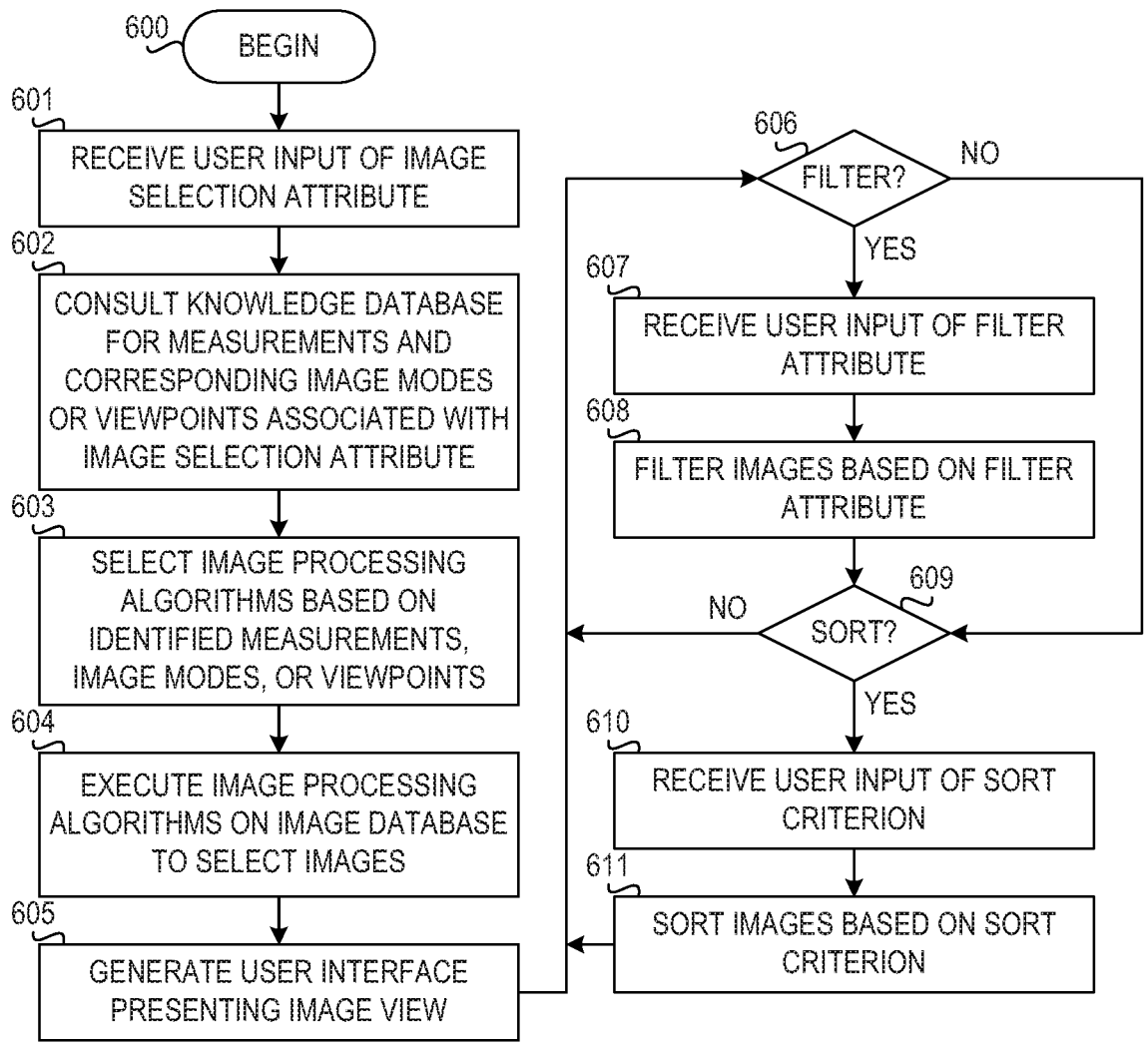
FIG. 6 is a flowchart illustrating operation of a mechanism for intelligently organizing displays of medical imaging content for rapid browsing and report creation in accordance with an illustrative embodiment.

FIG. 6 is a flowchart illustrating operation of a mechanism for intelligently organizing displays of medical imaging content for rapid browsing and report creation in accordance with an illustrative embodiment. Operation begins (block 600), and the mechanism receives user input of an image selection attribute (block 601). The user input may be text entered via a text input field or other user input method. Alternatively, the user input may be selection of a disease or abnormality from a drop-down list. Search based on abnormalities are not limited to the abnormalities found in a previous report. When studying a new imaging study, there is not report about it and the study is supposed to produce that report. Thus, the mechanism enables the user to search images based on abnormalities, disease, or measurements from a predetermined long list or using a search bar if it is more appropriate.

Next, the mechanism consults a knowledge database for measurements and corresponding image modes or viewpoints associated with the image selection attribute (block 602). The mechanism then selects image processing algorithms to find the mode, view point or valve (block 603). As mentioned above, the selected image processing algorithms can be pre-processed, and the results can be saved. Therefore, at execution time, in some cases, the task may search and retrieval without any image processing. The mechanism executes the image processing algorithms on an image database to select images (block 604). Then, the mechanism generates a user interface presenting an image view including the selected images (block 605).

The mechanism determines whether the user wishes to filter the presented images (block 606). If the user wishes to filter the images, then the mechanism receives user input of the filtering attribute, such as a mode or viewpoint (block 607). The mechanism filters the images based on the filter attribute (block 608).

Thereafter, or if the user does not wish to filter the images in block 606, the mechanism determines whether the user wishes to sort the images (block 609). If the user does wish to sort the images, then the mechanism receives user input of a sort criterion (block 610) and sorts the images based on the sort criterion (block 611). Thereafter, or if the user does not wish to sort the images in block 609, operation returns to block 606.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising a processor and a memory, the memory comprising instructions that are executed by the processor to specifically configure the processor to implement an intelligent medical image viewing engine, the method comprising:

generating, by a user interface generation component executing within the intelligent medical image viewing engine, an image viewing user interface comprising a plurality of filter attribute user interface elements and a sorting criteria user interface element;

receiving, by the intelligent medical image viewing engine via the image viewing user interface, a user input specifying at least one filter attribute and a sorting criterion for generating a medical image output, wherein the at least one filter attribute comprises a medical abnormality or a medical disease;

receiving, by the intelligent medical image viewing engine executing in the data processing system, a medical imaging study data structure comprising a plurality of electronic medical images from a medical image database;

analyzing, by an image processing component executing within the intelligent medical image viewing engine, the medical imaging study data structure to identify, for each electronic medical image in the plurality of electronic medical images, a corresponding set of image attributes, wherein analyzing the medical imaging study data structure comprises:

consulting a medical knowledge database to identify imaging modes or viewpoints that correspond to the medical abnormality or medical disease;

selecting, by an algorithm selection component executing within the intelligent medical image viewing engine, one or more image processing algorithms from an image processing database based on the identified imaging modes or viewpoints; and applying, by an image processing component executing within the intelligent medical image viewing engine, the one or more image processing algorithms to the plurality of electronic medical images;

correlating, by the intelligent medical image viewing engine, the at least one filter attribute with at least one medical attribute of medical images to be used for selection of electronic medical images from the medical imaging study data structure;

selecting, by an image selection component executing within the intelligent medical image viewing engine, a subset of the electronic medical images in the plurality of electronic medical images based on the correlation of the at least one filter attribute with the at least one medical attribute;

generating, by a user interface generation component executing within the intelligent medical image viewing engine, a medical image output comprising the subset of electronic medical images based on the selection, wherein generating the medical image output comprises sorting the subset of electronic medical images according to the sort criterion; and outputting, by the user interface generation component, the medical image output via the image viewing user interface.

2. The method of claim 1, wherein the at least one filter attribute further comprises at least one of a mode, viewpoint, or valve.

3. The method of claim 1, wherein correlating the at least one filter attribute with the at least one medical attribute comprises:

performing a lookup operation of the at least one filter attribute in the medical knowledge database, wherein the medical knowledge database maps filter attributes to medical attributes of medical images; and selecting a medical attribute based on results of the lookup operation.

4. The method of claim 1, wherein the one or more image processing algorithms comprise machine learning algorithms using the image data as input.

5. The method of claim 1, wherein the one or more image processing algorithms comprise image processing algorithms using image data as input.

6. The method of claim 1, wherein receiving the user input specifying the at least one filter attribute comprises receiving the user input from a search field user interface component.

7. The method of claim 1, wherein receiving the user input specifying the at least one filter attribute comprises receiving the user input from a drop-down list user interface component.

8. The method of claim 1, wherein the sort criterion comprises a mode, a viewpoint, or a valve.

9. A computer program product comprising a non-transitory computer readable storage medium having a computer readable program stored therein, wherein the computer readable program, when executed on at least one processor of a data processing system, causes the data processing system to implement an intelligent medical image viewing engine, wherein the computer readable program causes the data processing system to:

generate, by a user interface generation component executing within the intelligent medical image viewing engine, an image viewing user interface comprising a plurality of filter attribute user interface elements and a sorting criteria user interface element;

receive, by the intelligent medical image viewing engine via the image viewing user interface, a user input specifying at least one filter attribute and a sorting criterion for generating a medical image output, wherein the at least one filter attribute comprises a medical abnormality or a medical disease;

receive, by the intelligent medical image viewing engine executing in the data processing system, a medical imaging study data structure comprising a plurality of electronic medical images from a medical image database;

analyze, by an image processing component executing within the intelligent medical image viewing engine, the medical imaging study data structure to identify, for each electronic medical image in the plurality of electronic medical images, a corresponding set of image attributes, wherein analyzing the medical imaging study data structure comprises:
consulting a medical knowledge database to identify imaging modes or viewpoints that correspond to the medical abnormality or medical disease;
selecting, by an algorithm selection component executing within the intelligent medical image viewing engine, one or more image processing algorithms from an image processing database based on the identified imaging modes or viewpoints; and
applying, by an image processing component executing within the intelligent medical image viewing engine, the one or more image processing algorithms to the plurality of electronic medical images;

correlate, by the intelligent medical image viewing engine, the at least one filter attribute with at least one medical attribute of medical images to be used for selection of electronic medical images from the medical imaging study data structure;

select, by an image selection component executing within the intelligent medical image viewing engine, a subset of the electronic medical images in the plurality of electronic medical images based on the correlation of the at least one filter attribute with the at least one medical attribute;

generate, by a user interface generation component executing within the intelligent medical image viewing engine, a medical image output comprising the subset of electronic medical images based on the selection, wherein generating the medical image output comprises sorting the subset of electronic medical images according to the sort criterion; and output, by the user interface generation component, the medical image output via the image viewing user interface.

10. The computer program product of claim 9, wherein the at least one filter attribute further comprises at least one of a mode, viewpoint, or valve.

11. The computer program product of claim 9, wherein correlating the at least one filter attribute with the at least one medical attribute comprises:
performing a lookup operation of the at least one filter attribute in the medical knowledge database, wherein the medical knowledge database maps filter attributes to medical attributes of medical images; and
selecting a medical attribute based on results of the lookup operation.

12. The computer program product of claim 9, wherein the one or more image processing algorithms comprise machine learning algorithms using the image data as input.

13. The computer program product of claim 9, wherein the one or more image processing algorithms comprise image processing algorithms using image data as input.

14. The computer program product of claim 9, wherein receiving the user input specifying the at least one filter attribute comprises receiving the user input from a search field user interface component.

15. The computer program product of claim 9, wherein receiving the user input specifying the at least one filter attribute comprises receiving the user input from a drop-down list user interface component.

16. The computer program product of claim 9, wherein the sort criterion comprises a mode, a viewpoint, or a valve.

17. An apparatus comprising:
a processor; and
a memory coupled to the processor, wherein the memory comprises instructions which, when executed by the processor, cause the processor to implement an intelligent medical image viewing engine, wherein the instructions cause the processor to:
generate, by a user interface generation component executing within the intelligent medical image viewing engine, an image viewing user interface comprising a plurality of filter attribute user interface elements and a sorting criteria user interface element;
receive, by the intelligent medical image viewing engine via the image viewing user interface, a user input specifying at least one filter attribute and a sorting criterion for generating a medical image output, wherein the at least one filter attribute comprises a medical abnormality or a medical disease;
receive, by the intelligent medical image viewing engine executing in the data processing system, a medical imaging study data structure comprising a plurality of electronic medical images from a medical image database;
analyze, by an image processing component executing within the intelligent medical image viewing engine, the medical imaging study data structure to identify, for each electronic medical image in the plurality of electronic medical images, a corresponding set of image attributes, wherein analyzing the medical imaging study data structure comprises:
consulting a medical knowledge database to identify imaging modes or viewpoints that correspond to the medical abnormality or medical disease;
selecting, by an algorithm selection component executing within the intelligent medical image viewing engine, one or more image processing algorithms from an image processing database based on the identified imaging modes or viewpoints; and
applying, by an image processing component executing within the intelligent medical image viewing engine, the one or more image processing algorithms to the plurality of electronic medical images;
correlate, by the intelligent medical image viewing engine, the at least one filter attribute with at least one medical attribute of medical images to be used for selection of electronic medical images from the medical imaging study data structure;
select, by an image selection component executing within the intelligent medical image viewing engine, a subset of the electronic medical images in the plurality of electronic medical images based on the correlation of the at least one filter attribute with the at least one medical attribute;
generate, by a user interface generation component executing within the intelligent medical image viewing engine, a medical image output comprising the subset of electronic medical images based on the selection, wherein generating the medical image output comprises sorting the subset of electronic medical images according to the sort criterion; and outputting, by the user interface generation component, the medical image output via the image viewing user interface.

18. The apparatus of claim 17, wherein correlating the at least one filter attribute with the at least one medical attribute comprises:

performing a lookup operation of the at least one filter attribute in the medical knowledge database, wherein the medical knowledge database maps filter attributes to medical attributes of medical images; and selecting a medical attribute based on results of the lookup operation.

19. The apparatus of claim 17, wherein the one or more image processing algorithms comprise machine learning algorithms using the image data as input.

20. The apparatus of claim 17, wherein the one or more image processing algorithms comprise image processing algorithms using image data as input.

\* \* \* \* \*